(12) United States Patent
Oskin et al.

(10) Patent No.: US 10,932,654 B2
(45) Date of Patent: Mar. 2, 2021

(54) DEVICES AND METHODS FOR SECURING AUXILIARY TOOLS TO MINIMALLY INVASIVE INTRODUCTION TOOLS

(71) Applicant: Boston Scientific Scimed, Inc., Maple Grove, MN (US)

(72) Inventors: Christopher L. Oskin, Grafton, MA (US); Michael Barenboym, Bedford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 677 days.

(21) Appl. No.: 15/356,227

(22) Filed: Nov. 18, 2016

(65) Prior Publication Data
US 2017/0143188 A1    May 25, 2017

Related U.S. Application Data
(60) Provisional application No. 62/258,143, filed on Nov. 20, 2015.

(51) Int. Cl.
*A61B 1/00* (2006.01)
*A61B 1/018* (2006.01)
(Continued)

(52) U.S. Cl.
CPC ........ *A61B 1/0014* (2013.01); *A61B 1/00128* (2013.01); *A61B 1/00133* (2013.01);
(Continued)

(58) Field of Classification Search
CPC .......................... A61B 1/0014; A61B 1/00128
(Continued)

(56) References Cited

U.S. PATENT DOCUMENTS

| 8,353,493 B2 | 1/2013 | Golden et al. |
| 2006/0135846 A1 | 6/2006 | Hunt |

(Continued)

FOREIGN PATENT DOCUMENTS

| JP | H03-29296 | 2/1991 |
| JP | H04-124101 | 11/1992 |

(Continued)

OTHER PUBLICATIONS

International Search Report and Written Opinion for International Application No. PCT/US2016/062864, dated Feb. 10, 2017 (10 pages).

*Primary Examiner* — Alexandra L Newton
*Assistant Examiner* — Rynae Boler
(74) *Attorney, Agent, or Firm* — Bookoff McAndrews, PLLC

(57) ABSTRACT

An endoscopic system may include an endoscope including a proximal end, a distal end, and an elongated sheath extending therebetween. The elongated sheath may define at least one lumen. The proximal end of the endoscope may include a handle operably coupled to a proximal portion of the elongated sheath. The endoscopic system also may include a clip coupled to the handle of the endoscope. The clip may include at least one retaining arm configured to receive a handle of an auxiliary tool. The at least one lumen may be configured to receive a distal portion of the auxiliary tool. Associated devices and methods are also disclosed.

16 Claims, 5 Drawing Sheets

(51) Int. Cl.
*A61B 1/015* (2006.01)
*A61B 1/07* (2006.01)

(52) U.S. Cl.
CPC .............. *A61B 1/018* (2013.01); *A61B 1/015* (2013.01); *A61B 1/07* (2013.01)

(58) Field of Classification Search
USPC .................................................. 600/104, 106
See application file for complete search history.

(56) References Cited

U.S. PATENT DOCUMENTS

| | | | |
|---|---|---|---|
| 2006/0252993 A1* | 11/2006 | Freed | A61B 1/0052 600/146 |
| 2010/0198006 A1 | 8/2010 | Greenburg et al. | |
| 2011/0099773 A1* | 5/2011 | Golden | A61B 1/0014 24/457 |
| 2014/0114126 A1 | 4/2014 | Dresher | |
| 2014/0223701 A1* | 8/2014 | Bean | A61B 1/00133 24/483 |
| 2015/0034783 A1 | 2/2015 | Golden et al. | |
| 2015/0164307 A1 | 6/2015 | Galperin et al. | |

FOREIGN PATENT DOCUMENTS

| | | | |
|---|---|---|---|
| JP | 2004-086208 | 3/2004 | |
| JP | 2004-358011 | 12/2004 | |
| JP | 2005-058749 | 3/2005 | |
| JP | 2006-167472 | 6/2006 | |
| JP | 2007151595 A * | 6/2007 | ......... A61B 1/00133 |
| JP | 2007151595 A | 6/2007 | |
| JP | 2007-519425 | 7/2007 | |
| WO | WO20130137372 | 9/2013 | |

\* cited by examiner

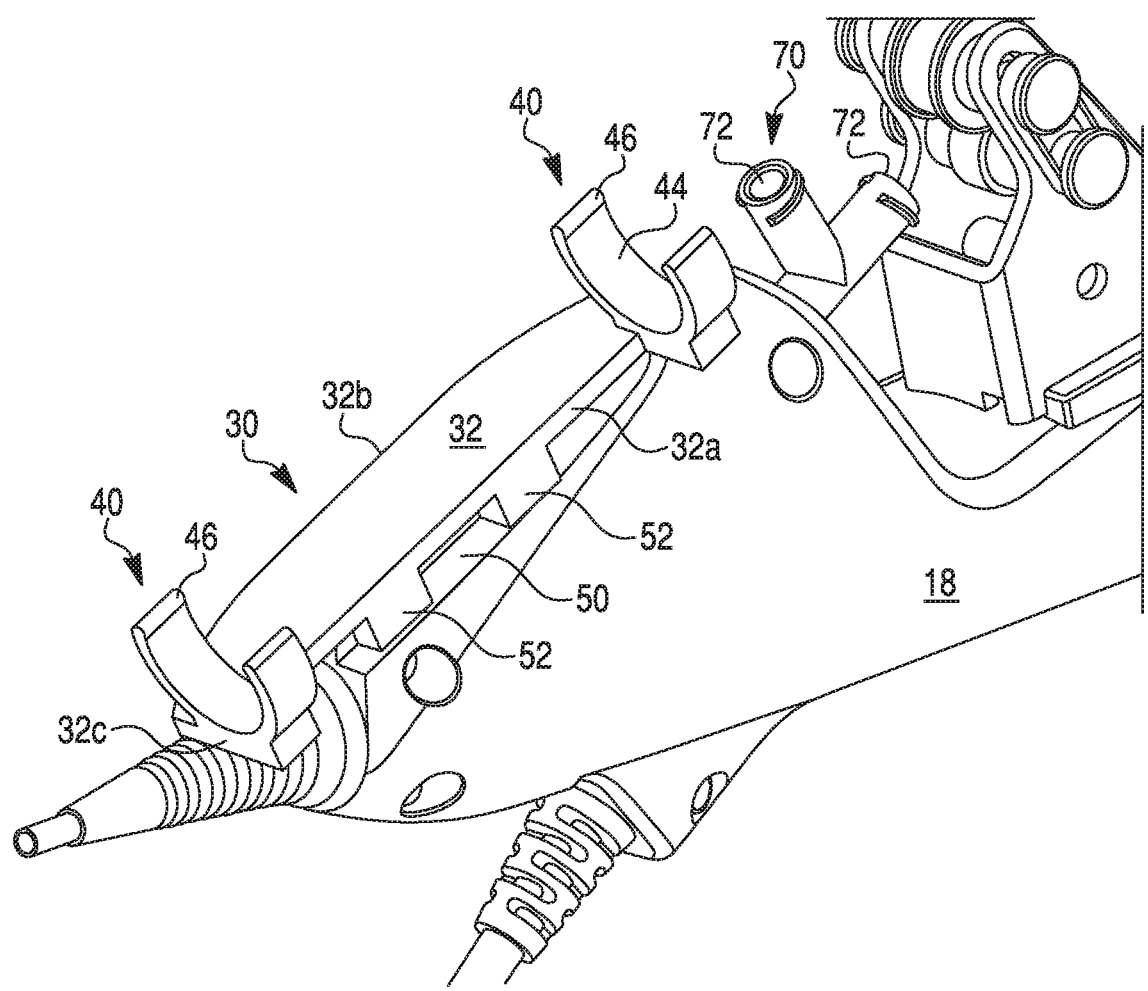

DEVICES AND METHODS FOR SECURING AUXILIARY TOOLS TO MINIMALLY INVASIVE INTRODUCTION TOOLS

CROSS-REFERENCE

This application claims the benefit of priority of U.S. Provisional Application No. 62/258,143, filed Nov. 20, 2015, the entirety of which is incorporated by reference into this application.

TECHNICAL FIELD

Aspects of the present disclosure generally relate to medical devices and procedures. In particular, aspects of the present disclosure relate to devices and methods for securing auxiliary tools to minimally invasive introduction tools.

BACKGROUND

Medical devices, such as endoscopes, or other suitable introduction devices, are employed for a variety of diagnostic and therapeutic procedures, such as laparoscopy, arthroscopy, gynoscopy, thoracoscopy, ureteroscopy, cystoscopy, etc. Endoscopes are known medical instruments having a handle, and a flexible tube extending from a distal end of the handle and configured for insertion into a body opening. The handle may include knobs and/or buttons to allow a first operator of the endoscope to manipulate a distal end portion of the flexible tube in a body passageway, to deliver air or water to the distal end portion of the flexible tube, to supply suction to the distal end portion of the flexible tube, to take images from the distal end portion of the flexible tube, etc.

The handle also may include a working channel opening which allows a second operator to hold a handle of an auxiliary device (such as a grasper, biopsy forceps, retrieval basket, or a snare) while inserting a distal end of the auxiliary device into the working channel opening. Once inserted into the endoscope's working channel, a distal portion of the auxiliary device may be positioned adjacent a distal end of the endoscope for performing one more diagnostic or therapeutic procedures. Thus, conventional endoscopes typically require two operators to perform procedures necessitating the use of an auxiliary tool. The use of two operators makes such procedures inefficient and expensive.

The present disclosure may address various shortcomings mentioned above and other shortcomings in the art.

SUMMARY

Examples of the present disclosure relate to, among other things, devices and methods for securing auxiliary tools to minimally invasive introduction tools. Each of the examples disclosed herein may include one or more of the features described in connection with any of the other disclosed examples.

In one example, an endoscopic system comprises an endoscope including a proximal end, a distal end, and an elongated sheath extending therebetween. The sheath may define at least one lumen, and the proximal end may include a handle operably coupled to a proximal portion of the sheath. The system may further comprise a clip coupled to the handle of the endoscope. The clip may have at least one retaining arm configured to receive a handle of an auxiliary tool. The at least one lumen defined by the sheath may be configured to receive a distal portion of the auxiliary tool.

Aspects of the system may additionally and/or alternatively include one or more of the features set forth below. The clip may be removably coupled to the handle of the endoscope. The clip may include a planar base. At least one retaining arm may extend away from the base. The at least one retaining arm may include a plurality of retaining arms. The plurality of retaining arms may include a first retaining arm, a second retaining arm, and a lateral side wall connecting the first and second retaining arms. Each of the plurality of retaining arms may have a semi-circular surface configured to receive the handle of the auxiliary tool. The at least one retaining arm may be configured to bend or flex. The at least one retaining arm may include a plurality of discrete arm portions. At least one of the plurality of discrete arm portions may be rotatably coupled to another of the plurality of discrete arm portions. At least a portion of the at least one retaining arm may include an elastomeric material configured to conform to the handle of the auxiliary tool. The at least one retaining arm may define a cavity for receiving the auxiliary tool. The cavity may include a central longitudinal axis offset from a longitudinal axis of the handle of endoscope. The central longitudinal axis of the cavity may be laterally offset from a center of the planar base. The system may include a geometric feature configured to retain the auxiliary tool in the cavity. The geometric feature may extend away from the least one retaining arm towards the central longitudinal axis. The handle of the endoscope may include a port in communication with the at least one lumen. The distal portion of the auxiliary tool may be configured for insertion into the port and the at least one lumen.

Another example is a clip for securing a handle of an auxiliary tool to a handle of an endoscope. The clip may include a planar base and at least one retaining arm extending away from the base to define a cavity including a central longitudinal axis offset from a center of the base. The at least one retaining arm may be configured to move relative to the central longitudinal axis of the cavity by bending of flexing. The at least one retaining arm may include an inner surface with at least one geometric feature extending toward the central longitudinal axis of the cavity.

Aspects of the clip may include one or more of the features set forth below. The at least one retaining arm may include a plurality of retaining arms. A lateral side wall may connect at least two of the plurality of retaining arms. The inner surface of the at least one retaining arm may define a semi-circular surface, and the least one geometric feature may extend away from the semi-circular surface toward the central longitudinal axis of the cavity. At least a portion of the inner surface may include an elastomeric material. At least one retaining arm may include a plurality of discrete arm portions. A hinge may be configured to rotatably couple at least one of the plurality of discrete arm portions to another of the plurality of discrete arm portions.

Yet another aspect is a method of securing a handle of an auxiliary tool to a handle of an endoscope. A method step may include removably securing a clip to the handle of the endoscope. The clip may include a planar base. At least one retaining arm may extend away from the base to define a cavity for receiving the handle of the auxiliary tool, and at least one geometric feature configured to retain the handle of the auxiliary tool within the cavity. The cavity may include a central longitudinal axis offset from a center of the base. The method may further include positioning the handle of the auxiliary tool within the cavity so as to engage the at least one geometric feature with the handle of the auxiliary tool.

In at least one aspect, the endoscope may have a proximal end, a distal end, an elongated sheath extending therebetween, and at least one lumen defined by the sheath, so that another method step may include inserting a distal portion of the auxiliary tool into the at least one lumen. Additionally, or alternatively, the handle of the endoscope may include a port in communication with the at least one lumen, so that another method step may include inserting the distal portion into the port.

It may be understood that both the foregoing general description and the following detailed description are exemplary and explanatory only and are not restrictive of the disclosure, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 2A-2C depict various views of an exemplary auxiliary tool clip for use with the exemplary endoscopic device of FIG. 1.

DETAILED DESCRIPTION

Reference will now be made in detail to examples of the present disclosure described above and illustrated in the accompanying drawings. Wherever possible, the same reference numbers will be used throughout to refer to the same or like parts.

The terms "proximal" and "distal" are used herein to refer to the relative positions of the components of an exemplary medical device. When used herein, "proximal" refers to a position relatively closer to the exterior of the body or closer to a user using the medical device. In contrast, "distal" refers to a position relatively further away from the user using the medical device, or closer to the interior of the body.

Though the following disclosure refers to "endoscope," "endoscopic," or "endoscopy," the principles/aspects described herein may be used with any suitable introduction sheath or device, even if such introduction sheath or device does not include one or more features typically associated with "endoscopes."

Figure 1:
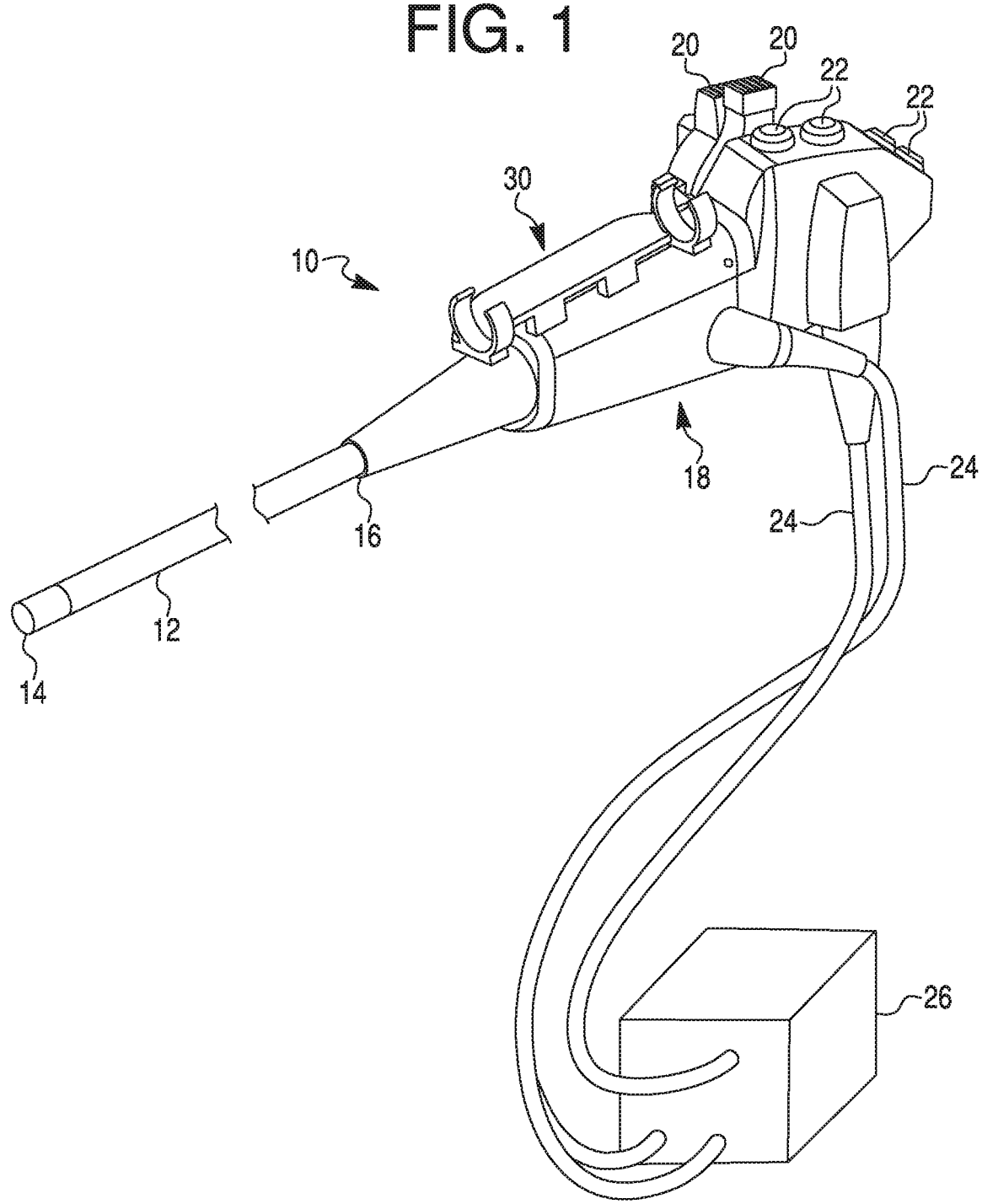
FIG. 1 depicts an isometric view of an exemplary endoscopic device for use in conjunction with aspects of the present disclosure.
Figure 2A:
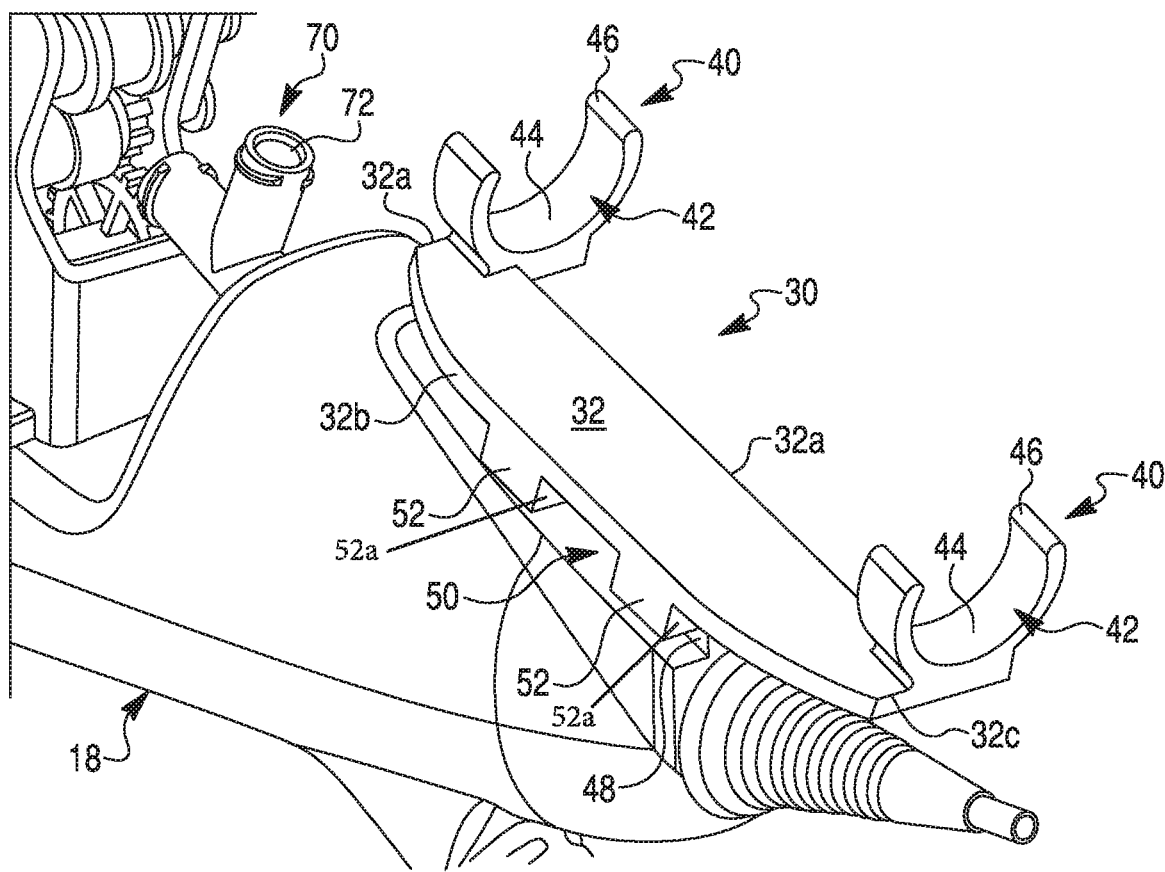

With reference now to FIG. 1, an endoscope 10 may include a flexible, elongated insertion tube 12 extending from a distal end 14 to a proximal end 16. The proximal end 16 may be attached to a control handle 18 containing or more actuators 20, 22. The actuators 20, 22 may be operably coupled to a conventional, external control unit 26 through one or more cable(s) 24. Control unit 26 may be configured to deliver a fluid or supply suction to distal end 14 via cable(s) 24. Cable(s) 24 also may include means for providing illumination (not shown in FIG. 1) at distal end 14 of the insertion tube 12. For example, the cable 24 may contain a first fiber optic bundle which couples illumination from the unit 26 through a fiber optic bundle in the insertion tube 12 to an illumination window at the distal end 14. Similarly, cable 24 may include a second fiber optic bundle for transmitting light that forms images from the distal end 14 to unit 26. Further, as shown in FIGS. 2A-3, control handle 18 may include one more ports 70 leading to one or more working channels disposed within elongate insertion tube 12. Each port 70 may include one or more openings 72 providing access to the working channels within insertion tube 12. As will be described in greater detail below, the working channel(s) may be used to facilitate insertion of an auxiliary tool (e.g., laser fiber, grasper, biopsy forceps, retrieval basket, or a snare) through insertion tube 12 for positioning adjacent distal end 14 and performing one or more diagnostic and/or therapeutic procedures. To facilitate use of the auxiliary tool, handle 18 may include a clip 30 configured to secure a handle of the auxiliary tool to handle 18, as will be described in greater detail below.

Clip 30 may be made of any suitable materials, such as, e.g., plastic, polymers, Polytetrafluoroethylene (PTFE), and/or expanded PTFE (ePTFE). Moreover, clip 30 may be fabricated via any suitable manufacturing process, including, but not limited to, molding and extrusion.

Figure 2C:
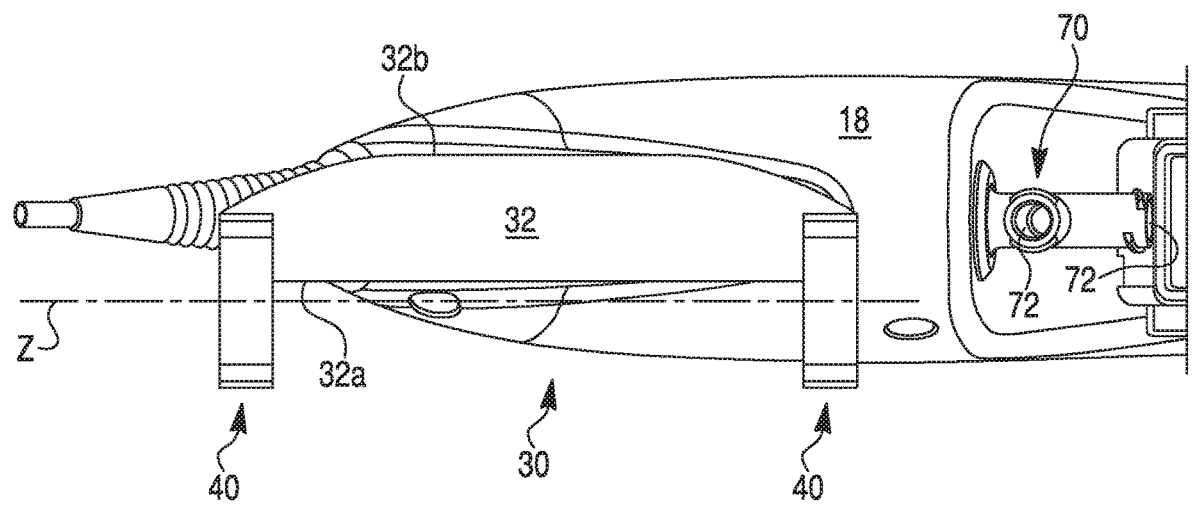
Figure 3:
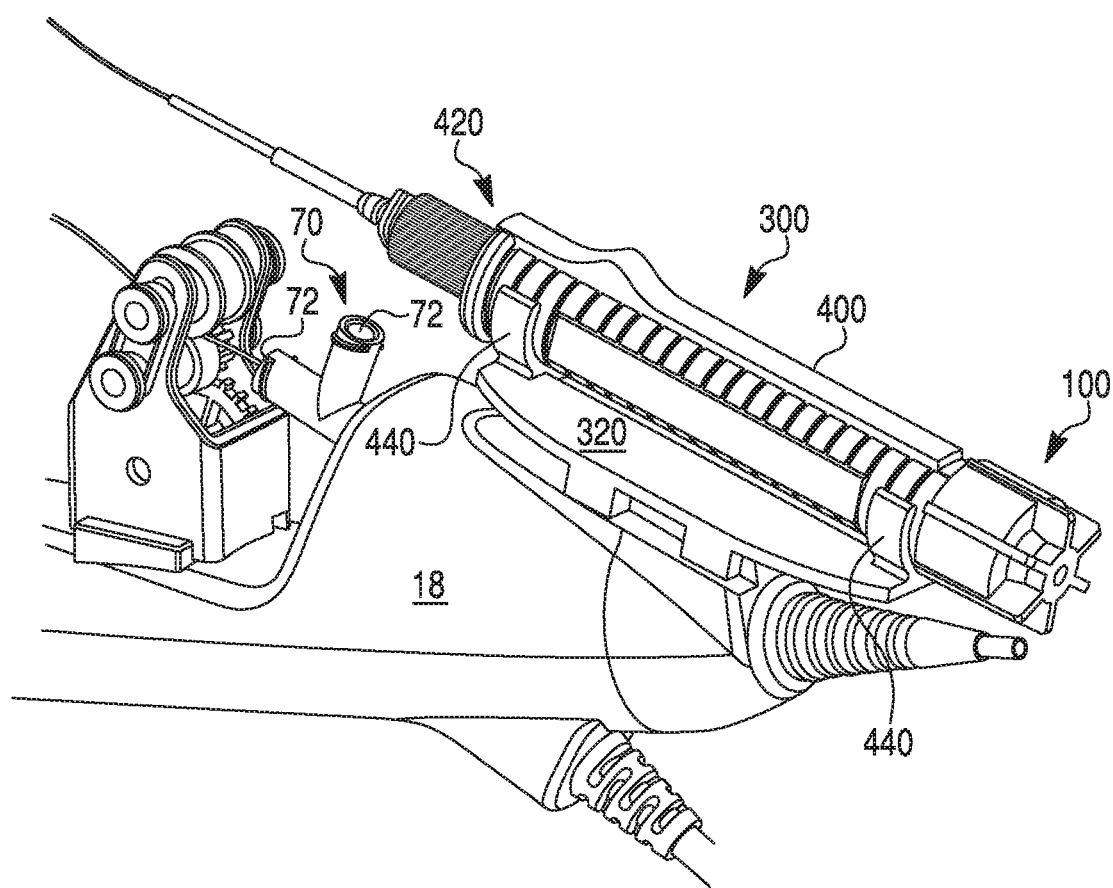
FIG. 3 depicts another exemplary aspect of an auxiliary tool clip for use with the exemplary endoscopic device of FIG. 1.

With reference now to FIGS. 2A-2C, multiple views of clip 30 are depicted. Clip 30 may include a base 32. Base 32 may include any suitable shape, configuration, and/or dimension. It is contemplated that the shape, configuration, and/or dimensions of base 32 at least may be dependent on the configuration of handle 18 and/or a handle of a desired auxiliary tool. In one aspect, base 32 may include a substantially planar or flat configuration. As shown in FIG. 2A, base 32 may include a substantially D-shaped configuration. For example, base 32 may include a first substantially straight side 32a joined to a second substantially curved side 32b by short sides 32c. Base 32 may include any suitable thickness desired. It is contemplated that base 32 may include a thickness capable of providing base 32 with sufficient rigidity to support a handle of an auxiliary tool. Base 32 may include a planar, unitary construction. Alternatively, base 32 may include any desired geometric features, such as, e.g., one or more through openings, one or more surface features (scoring, depressions, protrusions, etc.), and/or one or more geometric features (e.g., notches, scallops, protrusions, etc.) in any of sides 32a, 32b, and/or 32c.

Clip 30 also may include one or more receiving or retaining arms 40 disposed along side 32a. Though the depicted aspects of the present disclosure only include two receiving arms 40, base 32 may include any suitable number of receiving arms 40. Further, it is contemplated that each receiving arm 40 may be substantially similar to the other receiving arm(s) 40 of clip 30. Thus, for the purposes of brevity, only one receiving arm 40 will be described herein. However, in at least one aspect, at least one of receiving arms 40 may be different than the other receiving arm(s) 40. Furthermore, in those aspects where more than one receiving arms 40 are provided on base 32, a portion of each receiving arm 40 may be connected to a corresponding portion of an adjacent receiving arm 40, such that the connection between the adjacent receiving arms 40 defines a lateral wall adjacent a cavity 42.

With continuing reference to FIGS. 2A-2C, receiving arm 40 may include a substantially semi-circular configuration defining a longitudinal axis Z (FIG. 2C). Those of ordinary skill will readily recognize that receiving arm 40 may include any suitable geometric configuration. For example, receiving arm 40 may define a substantially polygonal configuration. As alluded to above, receiving arm 40 may extend from side 32a such that axis Z is spaced away from side 32a, as shown in FIG. 2C. In some aspects, receiving arm 40 may extend from side 32a such that axis Z is disposed in the same vertical plane as side 32a. In any event, it is contemplated that axis Z is spaced from a central longitudinal axis of base 32. Moreover, in some aspects, axis Z may be offset from a central longitudinal axis of the endoscope handle 18 and/or introduction sheath 12. Such positioning of axis Z facilitates easier control for left handed versus right handed operators. As will be described below, clip 30 may be removably secured to handle 18. Consequently, clip 30 may be reoriented on handle 18 such that axis Z is spaced away from the central longitudinal axis of base 32 in a direction opposite to that depicted in FIGS. 2A-2C.

Receiving arm 40 may define a cavity 42 (FIG. 2A) for receiving a portion (e.g., a handle) of an auxiliary tool. Though FIGS. 2A-2C depict cavity 42 as including a substantially semi-circular or curvilinear configuration, cavity 42 may include any suitable configuration, including, but not limited, to a polygonal configuration. Receiving arm 40 may extend approximately 180 degrees around axis Z. In some aspects, receiving arm 40 may extend between approximately 45 degrees and 360 degrees around axis Z. In aspects where receiving arm 40 extends 360 degrees around axis Z, receiving arm 40 may define a substantially closed cavity 42 for receiving a handle of an auxiliary tool. In one exemplary aspect, receiving arm 40 may extend greater than 90 degrees (e.g., approximately 270 degrees) about axis Z. As used herein, the term "approximately" is understood to convey a measure that is +/−10% of the stated value. Those of ordinary skill in the art will understand that when receiving arm 40 extends less than 360 degrees around axis Z, a space may be provided between opposing ends of receiving arm 40 to, e.g., allow reciprocal motion of an actuator associated with the handle of the auxiliary tool.

In aspects where receiving arm 40 extends more than 180 degrees around axis Z, receiving arm 40 may elastically deform so to allow insertion of the handle of an auxiliary tool. That is to say, opposing ends of receiving arm 40 may be forced away from each other so to allow the handle of an auxiliary tool to be passed into cavity 42. The opposing ends of receiving arm 40 may move towards each other after the handle of auxiliary tool is in cavity 42, due to the elasticity of receiving arm 40. Alternatively, a user may urge opposing ends of receiving arm 40 toward one another. Further, though receiving arm 40 is depicted as having a one-piece or unitary construction, receiving arm 40 may include a plurality of discrete arm portions (not shown) coupled to one another by, e.g., a hinge mechanism (not shown) configured to allow adjacent arm portions to move relative to one another. For example, in one aspect, receiving arm 40 may include two discrete arm portions (not shown). The two discrete arm portions may be coupled together at one end via a hinge such that an opposite end of each arm portion may be moved away from the other arm portion to provide a passageway into cavity 42. In some aspects, the discrete arm portions may be biased towards one another by a spring so as to facilitate retaining a handle received within cavity 42.

As shown in, e.g., FIG. 2A, cavity 42 may be defined by an inner surface 44 of receiving arm 40. Inner surface 44 may include one or more geometric features (e.g., protrusions) configured to receive and retain the handle of an auxiliary tool. In the example shown in FIGS. 2A-2B, terminal ends of receiving arm 40 may include raised ramps 46. That is to say, ramps 46 may extend away from inner surface 44 and into cavity 42 so as to retain a handle received in cavity 42. In other aspects, inner surface 44 may include an elastomeric coating configured to frictionally retain a handle within cavity 42. In further aspects, it is contemplated that a substantial portion (e.g., greater than 50%) of receiving arm 40 may be made of an elastomeric material that allows receiving arm 40 to flex and conform to handles of varying sizes. To ensure a handle receiving within cavity 42 is retained therein, some aspects of clip 30 may include a strap (not shown) configured to extend, e.g., from side 32b, over the received handle, and secured to side 32a, or vice versa. Additionally or alternatively, a strap may extend across the gap between free ends of receiving arm 40.

With continuing reference to FIGS. 2A-2C, clip 30 may be removable secured to handle 18 by any suitable mechanism. However, in some aspects, clip 30 may be fixedly secured to handle 18. In such aspects, clip 30 may be formed of a one-piece construction with handle 18. In those aspects where clip 30 is removable from handle 18, handle 18 may include one or more geometric features configured to receive, orient, and/or secure clip 30 on handle 18. In one example, handle 18 may include a vertical spline 48 and adjacent groove(s) 50 configured to receive clip 30. Clip 30 also may include one or more corresponding geometric features configured to secure clip 30 on handle 18. For example, clip 30 may include a longitudinal channel 52a configured to receive spline 48 therein, such that clip 30 may slide onto handle 18. Longitudinal channel 52a of clip 30 may be defined by one or more side walls 52, as shown in FIGS. 2A-2B. Longitudinal channel 52a of clip 30 and spline 48 may form, for example, a sliding dovetail joint. Additionally or alternatively, one or more surfaces of side walls 52 on one or both sides of longitudinal channel. 52a, may engage one or more surface of spline 48, such that side walls 52 and spline 48 may form a snap-fit connection. This may allow clip 30 to be mounted on handle 18 along a direction normal to the surface of handle 18 on which spline 48 is formed.

In some aspects, one or more locking features may be provided on clip 30 and/or handle 18 to prevent clip 30 from sliding off of spline 48. For example, longitudinal channel 52a of clip 30 may include a protrusion (not shown) configured to engage a depression (not shown) on spline 48 to facilitate retaining clip 30 on handle 18. Those of ordinary skill in the art will readily recognize that the aforementioned mechanism for securing clip 30 on handle 18 may be reversed and/or replaced with any other suitable mechanism.

With reference now to FIG. 3, there is depicted another exemplary aspect of a clip 300 in accordance with the present disclosure. Clip 300 may include any of the features described above in connection with clip 30. In some aspects, however, clip 300 may define an elongated channel 420 for receiving a handle 100 of an auxiliary tool. Elongated channel 420 may be defined by a curved lateral side wall 400 extending away from base 320 in a first direction and one or more arm(s) 440 extending away from base 320 in a second direction opposite the first direction. In use, the curved lateral side wall 400 may extend around a first side of handle 100 and the arm(s) 440 may extend another side of handle 100. Though the depicted aspect includes two arms 440, those of ordinary skill in the art will recognize that a greater or lesser number of arms may be provided without departing from the principles of the present disclosure.

The curved lateral side wall 400 may extend approximately 180 degrees around handle 100 in the first direction from base 320. One or more of arms 440 may extend approximately 45 degrees around handle 100 in the second direction from base 320. Though both arms 440 are shown as extending approximately the same number of degrees around handle 100, each arm 400 may extend a differing number of degrees around handle 100. The curved lateral side wall 400 may further include one or more geometric features (e.g., a protrusion) to assist with gripping and/or moving curved lateral side 400 away from arms 440, so as to release handle 100 from clip 300.

With renewed reference to FIGS. 1-3, one exemplary method of using clip 30/300 now will be described. Either prior to or after positioning insertion tube 12, a user may advance a distal end of an auxiliary tool (e.g., a retrieval basket or snare) into an opening 72 of port 70 and through a working channel of endoscope 10. To eliminate the need for having two operators, the user may secure clip 30 to handle 18 (if not already secured) and dispose handle 100 of the auxiliary tool within cavity 42/channel 420 so that handle 100 may be retained by clip 30/300 on handle 18.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. An endoscopic system, the system comprising:
    an endoscope including a proximal end, a distal end, and an elongated sheath extending therebetween, the sheath defining at least one lumen, and the proximal end including a handle operably coupled to a proximal portion of the sheath; and
    a clip including (1) a longitudinally-extending channel defined by a pair of sidewalls, and (2) a plurality of retaining arms configured to receive a handle of an auxiliary tool, wherein the clip is coupled to the handle of the endoscope via the channel,
    wherein the at least one lumen is configured to receive a distal portion of the auxiliary tool, and
    wherein at least one retaining arm from the plurality of retaining arms extends distally of a distalmost sidewall of the pair of sidewalls.

2. The endoscopic system of claim 1, wherein the clip includes a planar base and is removably coupled to the handle of the endoscope, wherein the at least one retaining arm from the plurality of retaining arms extends away from the planar base, and wherein the at least one retaining arm from the plurality of retaining arms is configured to bend or flex.

3. The endoscopic system of claim 1, wherein the plurality of retaining arms includes a first retaining arm, a second retaining arm, and a lateral side wall connecting the first and second retaining arms.

4. The endoscopic system of claim 3, wherein each of the first retaining arm and the second retaining arm has a semi-circular surface configured to receive the handle of the auxiliary tool.

5. The endoscopic system of claim 1, wherein at least a portion of each retaining arm from the plurality of retaining arms includes an elastomeric material configured to conform to the handle of the auxiliary tool.

6. The endoscopic system of claim 1, wherein each retaining arm from the plurality of retaining arms defines a cavity for receiving the auxiliary tool, the cavity including a central longitudinal axis offset from a longitudinal axis of the handle of endoscope.

7. The endoscopic system of claim 6, wherein the central longitudinal axis of the cavity is laterally offset from a center of a planar base.

8. A clip for securing a handle of an auxiliary tool to an endoscope, the clip comprising:
    a planar base;
    a first lateral sidewall being substantially straight;
    a second lateral side wall, opposite the first side wall, being substantially curved; and
    a plurality of retaining arms disposed on the first lateral side wall of the clip and extending away from the base to define a cavity including a central longitudinal axis offset from a center of the base; and
    a longitudinal channel defined by a plurality of sidewalls,
    wherein the plurality of retaining arms includes a first retaining arm and a second retaining arm connected by the planar base,
    wherein the first retaining arm is disposed proximally to a proximalmost sidewall of the plurality of sidewalls,
    wherein the second retaining arm is disposed distally to a distalmost sidewall of the plurality of sidewalls,
    wherein at least one retaining arm from the plurality of retaining arms is configured to bend or flex relative to the central longitudinal axis.

9. The clip of claim 8, wherein the inner surface of the at least one retaining arm from the plurality of retaining arms defines a semi-circular surface.

10. The clip of claim 8, wherein at least a portion of the inner surface of the at least one retaining arm from the plurality of retaining arms includes an elastomeric material.

11. The endoscopic system of claim 1, wherein the handle includes a groove, and wherein the clip includes at least one sidewall configured to be snap-fit to the groove.

12. The endoscopic system of claim 11, wherein the at least one sidewall extends away from the clip in a direction opposite a direction of extension of the at least one retaining arm.

13. The endoscopic system of claim 1, wherein the clip is fixedly coupled to the handle of the endoscope such that the clip is fixedly secured with respect to the handle.

14. The endoscopic system of claim 1, wherein the clip includes a planar base including a first side being substantially straight and perpendicular to a direction of extension of the plurality of retaining arms, and a second side, opposite the first side, being substantially curved.

15. The endoscopic system of claim 1, wherein at least one retaining arm from the plurality of retaining arms extends proximally of the one or more sidewalls.

16. The endoscopic system of claim 1, wherein a first retaining arm from the plurality of retaining arms is disposed at a proximal end of the clip, a second retaining arm from the plurality of retaining arms is disposed at a distal end of the clip, and the one or more sidewalls are disposed entirely between the first retaining arm and the second retaining arm.

* * * * *